(12) United States Patent
Pera et al.

(10) Patent No.: US 8,278,105 B2
(45) Date of Patent: Oct. 2, 2012

(54) INDUCTION, PROPAGATION AND ISOLATION OF LIVER PROGENITOR CELLS

(75) Inventors: Martin F. Pera, Los Angeles, CA (US); Tracy L. Zinberg, Long Beach, CA (US); Kouichi Hasegawa, Pasadena, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 12/556,478

(22) Filed: Sep. 9, 2009

(65) Prior Publication Data

US 2010/0062527 A1 Mar. 11, 2010

Related U.S. Application Data

(60) Provisional application No. 61/095,494, filed on Sep. 9, 2008.

(51) Int. Cl.
*C12N 5/00* (2006.01)
*C12N 5/02* (2006.01)
*C12N 5/071* (2010.01)

(52) U.S. Cl. ............ 435/377; 435/366; 435/405

(58) Field of Classification Search .......... 435/377, 435/366, 405
See application file for complete search history.

(56) References Cited

FOREIGN PATENT DOCUMENTS

WO    WO 2007113505 A2 * 10/2007

OTHER PUBLICATIONS

Verfaillie et al. Hematology (Am Soc Hematol Educ Program). 2002;:369-91.*
Hoffman et al. Nature Biotech., 23(6): 699-708, 2005.*
Pera et al. Development, 131: 5515-5525, 2004.*
Song et al. Cell Res., 19(11): 1233-1242, 2009.*
English et al. Trends in Pharmcological Sciences, 23(1): 40-45, 2002.*
McCubrey et al. Exp. Opinion. Emerging Drugs, 15(2): 203-223, 2010.*
Graichen et al. Differentiation, 76(4): 657-70, 2008, Abstract only.*
Zhou et al. Chemistry & Biology, 17: 285-295, 2010.*
Tomescot. Stem Cells, 25: 2200-2205, 2007.*
Meijer et al. Trends in Pharm. Sciences, 25(9): 471-480, 2004.*
Wozney et al. Spine, 27: S2-S8, 2002.*
Canalis et al.(Endocrine Rev., 24(2): 218-235, 2003.*
Ying. Nature, 453: 519-524, 2008.*
Cai et al., Hepatology, 45: 4229-1239, 2007.*
Reubinoff, B.E., Embryonic stem cell lines from human blastocysts: somatic differentiation in vitro. Nature Biotechnology (Apr. 2000), 18(4):399-404.
Stamp, L. et al., A novel cellsurface marker found on human embryonic hepatoblasts and a subpopulation of hepatic biliary epithelial cells, Stem Cells (2005) (Dayton, Ohio) 23(1):103-112.
Ying, Q. et al., The ground state of embryonic stem cell self-renewal, Nature (May 2008), 453:519-523.

* cited by examiner

*Primary Examiner* — Thaian N Ton
(74) *Attorney, Agent, or Firm* — Seth D. Levy; Nixon Peabody LLP

(57) ABSTRACT

The present invention relates to methods of induction and isolation of progenitor cells from stem cell cultures, specifically liver progenitor cells from human embryonic stem cell cultures. In one embodiment, the present invention provides a method of inducing hepatocyte-like progenitor cells by placing a quantity of human embryonic stem cells in a medium supplemented with an inhibitor of the MAPK/MEK/ERK signaling pathway, FGFR, GSK3 and/or BMP.

21 Claims, 10 Drawing Sheets

HNF3 beta

Albumin

Sox-17

INDUCTION, PROPAGATION AND ISOLATION OF LIVER PROGENITOR CELLS

The present application claims the benefit of priority under 35 U.S.C. §119(e) of provisional application Ser. No. 61/095,494, filed Sep. 9, 2008, the contents of which are hereby incorporated by reference.

GOVERNMENT RIGHTS

This invention was made with government support under Contract No. P30 DK048522 awarded by the National Institutes of Health. The government has certain rights in the invention.

FIELD OF THE INVENTION

The invention relates generally to the field of stem cells and, more specifically, to the induction, propagation and isolation of progenitor cells of the liver.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

A stem cell is a cell type that has a unique capacity to renew itself and give rise to specialized or differentiated cells. Although most cells of the body are committed to conduct a specific function, a stem cell is uncommitted, until it receives a signal to develop into a specialized cell type. What makes the stem cells unique is their proliferative capacity, combined with their ability to become specialized. Somatic stem cells are present in the adult organism. Pluripotency tests have shown that whereas the embryonic or blastocyst-derived stem cells can give rise to all cells in the organism, including the germ cells, somatic stem cells have a more limited repertoire in descendent cell types.

To date, some studies have shown that human embryonic stem ("ES") cells can be induced to differentiate into cells with gene expression profiles characteristic of hepatocytes on a modest scale. However, there remains a need in the art for novel methods of actually inducing liver stem or progenitor cells from human ES cell culture. Large scale production of hepatocyte precursors from human ES cells has application in several key areas; for example, to enable in vitro studies of the pathogenesis of liver disease, such as viral hepatitis; to enable studies of the metabolism and toxicity of drugs in vitro, leading to better predictive toxicology tests; and to provide cells for transplantation therapy in liver diseases such as Hepatitis C, which is currently a worldwide epidemic affecting over 200 million patients.

Thus, there is a need in the art for novel methods of inducing liver progenitor cells from stem cells.

SUMMARY OF THE INVENTION

Various embodiments include a method of inducing and/or propagating a quantity of progenitor cells, comprising providing a quantity of human stem cells, and placing the quantity of human stem cells in a medium supplemented with one or more of an inhibitor of the mitogen-activated protein kinase (MAPK)/map-erk kinase (MEK)/extracellular signal-regulated kinase (ERK) signaling pathway, a fibroblast growth factor receptor (FGFR) inhibitor; and a glycogen synthase kinase 3 (GSK3) inhibitor. In another embodiment, the human stem cells are human embryonic stem cells. In another embodiment, the inhibitor of the MAPK/MEK/ERK signaling pathway comprises a compound of the formula:

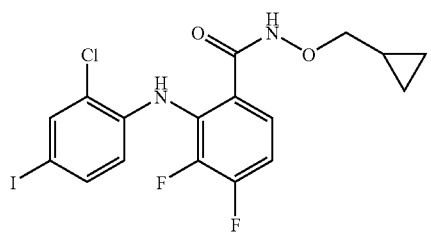

(Formula 1) or a pharmaceutical equivalent, analog, derivative and/or salt thereof. In another embodiment, the inhibitor of the MAPK/MEK/ERK signaling pathway comprises a compound of the formula:

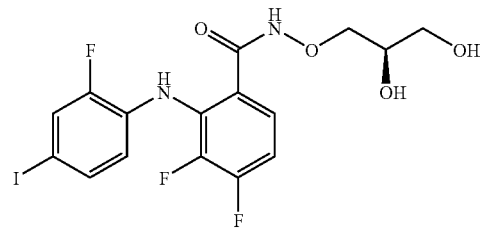

(Formula 2) or a pharmaceutical equivalent, analog, derivative and/or salt thereof. In another embodiment, the FGFR inhibitor comprises a compound of the formula:

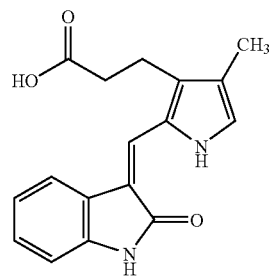

(Formula 3) or a pharmaceutical equivalent, analog, derivative and/or salt thereof. In another embodiment, the GSK3 inhibitor comprises a compound of the formula:

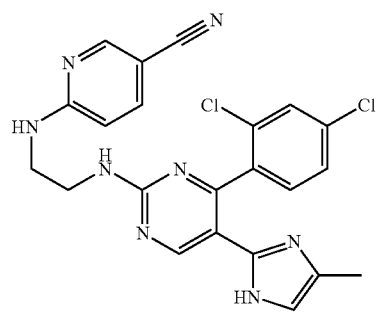

(Formula 4) or a pharmaceutical equivalent, analog, derivative and/or salt thereof. In another embodiment, the progenitor cells are hepatocyte-like. In another embodiment, the stem cell comprises human embryonic stem cell 2 (HES2) and/or human embryonic stem cell 3 (HES3). In another embodiment, the medium comprises 0.2 to 3.0 µM of the inhibitor of the MAPK/MEK/ERK signaling pathway. In another embodiment, the medium comprises 1.0 to 6.0 µM of the FGFR inhibitor. In another embodiment, the medium comprises 1.0 to 6.0 µM of the GSK3 inhibitor. In another embodiment, the medium is further comprising a bone morphogenetic protein (BMP) inhibitor. In another embodiment, the medium comprises 1.0 to 6.0 µM of the BMP inhibitor. In another embodiment, the BMP inhibitor comprises dorsomorphin.

Other embodiments include a composition comprising an inhibitor of the MAPK/MEK/ERK signaling pathway, an FGFR inhibitor, a GSK3 inhibitor, and a BMP inhibitor.

Various embodiments also include a composition comprising activin, BMP, epidermal growth factor (EGF), heregulin, fibroblast growth factor 1 (FGF-1), insulin growth factor (IGF), vascular endothelial growth factor (VEGF), angiopoietin, and transforming growth factor beta (TGF beta).

Other embodiments include a composition, comprising a quantity of progenitor cells, produced by the process providing a quantity of human stem cells, and placing the quantity of human stem cells in a medium supplemented with one or more of an inhibitor of the mitogen-activated protein kinase (MAPK)/map-erk kinase (MEK)/extracellular signal-regulated kinase (ERK) signaling pathway, a fibroblast growth factor receptor (FGFR) inhibitor, and a glycogen synthase kinase 3 (GSK3) inhibitor.

Other features and advantages of the invention will become apparent from the following detailed description, taken in conjunction with the accompanying drawings, which illustrate, by way of example, various embodiments of the invention.

BRIEF DESCRIPTION OF THE FIGURES

FIG. 1 shows that the large cells do not express pluripotency markers, but express markers of definitive endoderm (Sox-17), extraembryonic endoderm (Sox-7, Gata-4, AFP), and gut derivatives (Pax-6, pancreas; Cdx-2, intestine; albumin, liver; FoxA2 and HNF-6, liver progenitors).

DESCRIPTION OF INVENTION

Figure 1A:
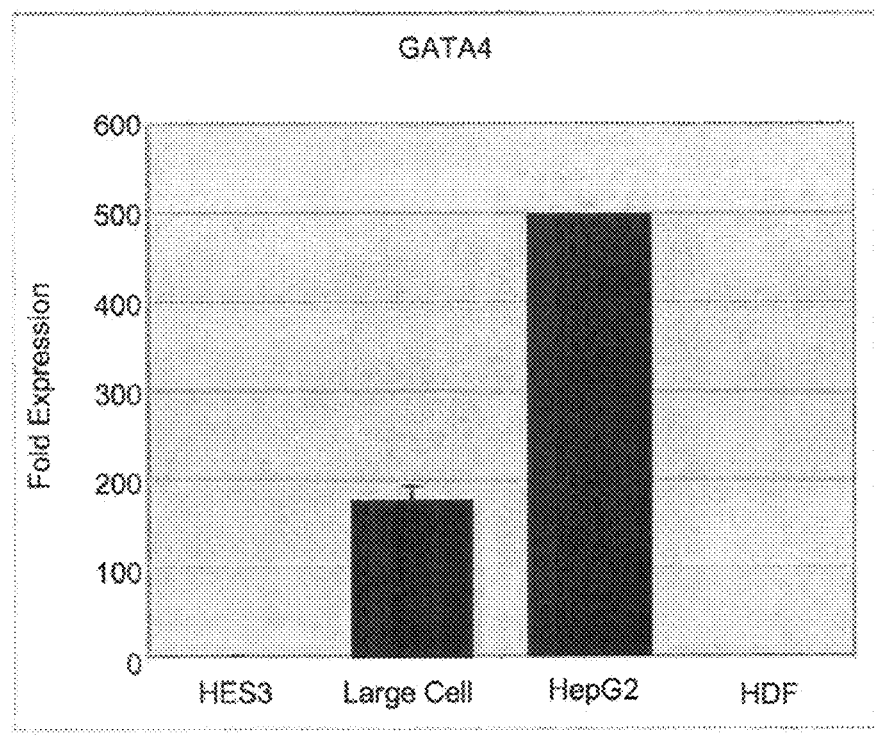
FIG. 1 depicts, in accordance with an embodiment herein, charts of gene expression in induced cells.
Figure 1B:
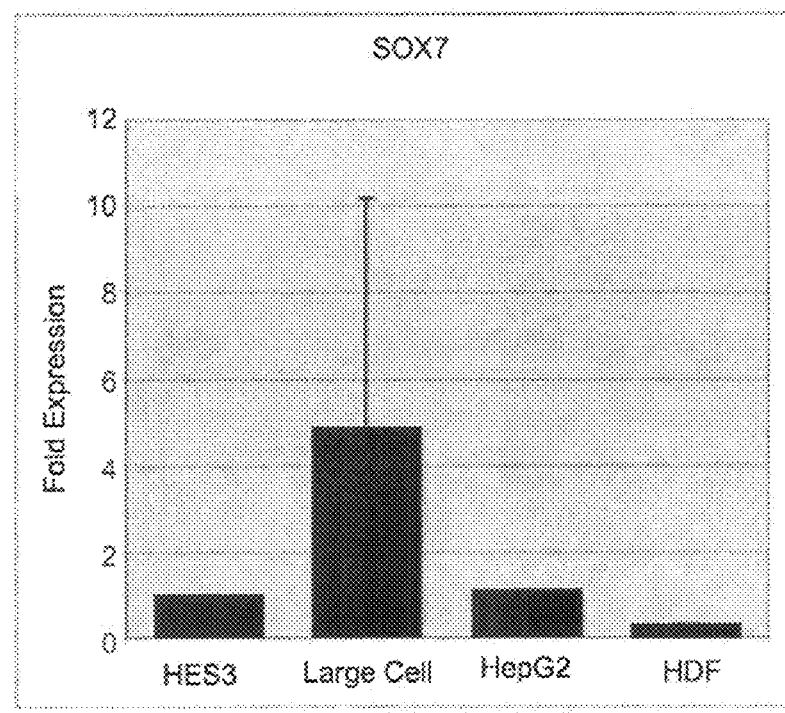
Figure 1C:
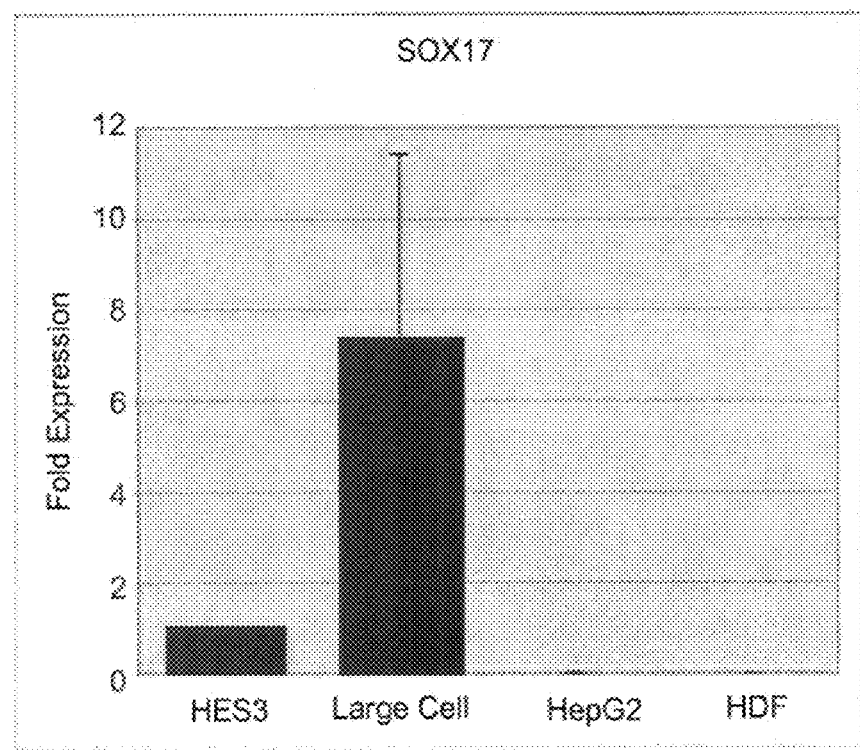
Figure 1D:
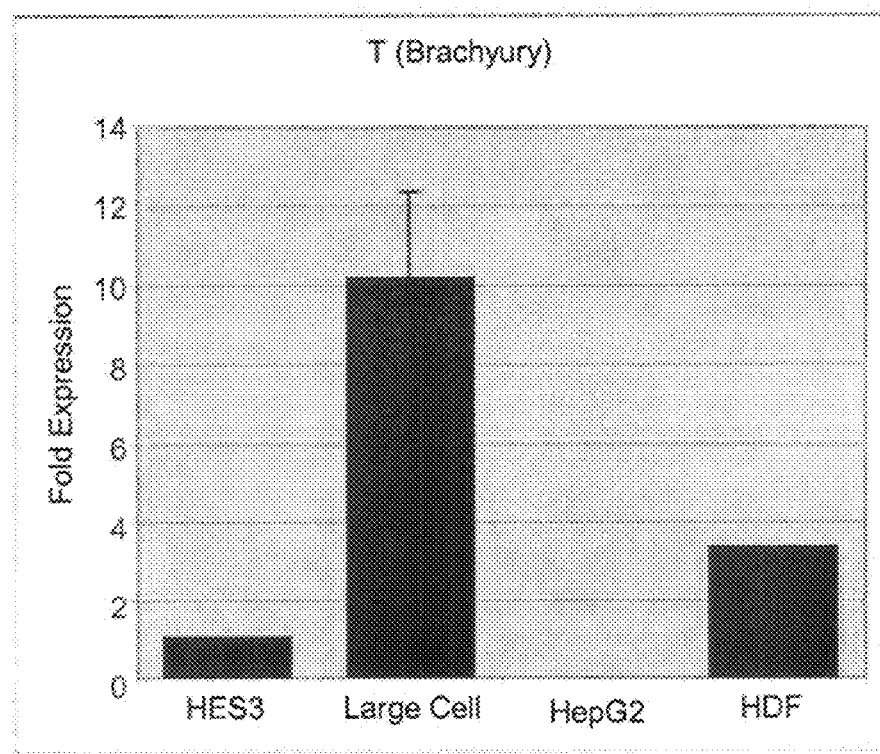
Figure 1E:
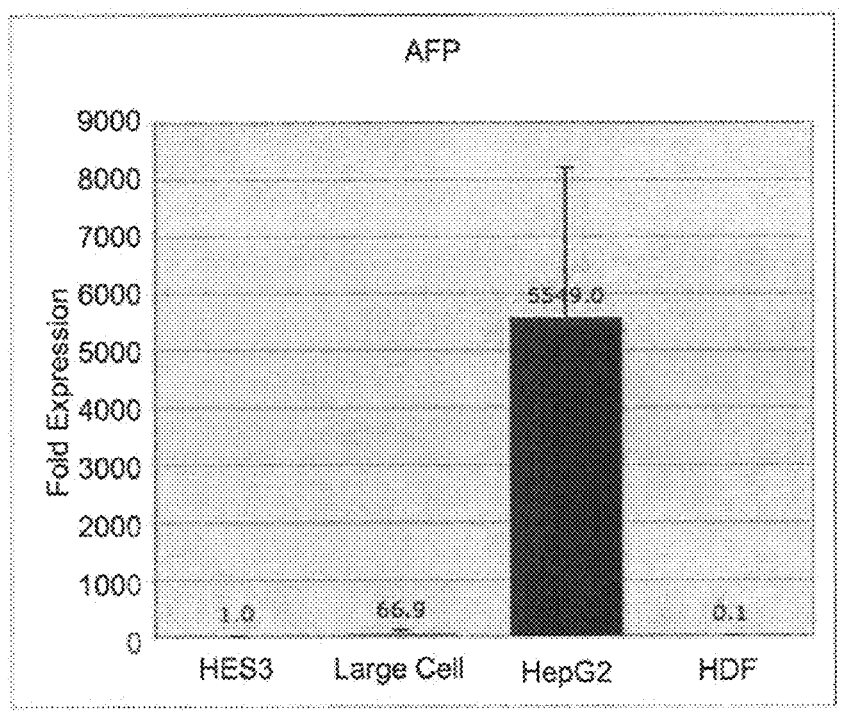
Figure 1F:
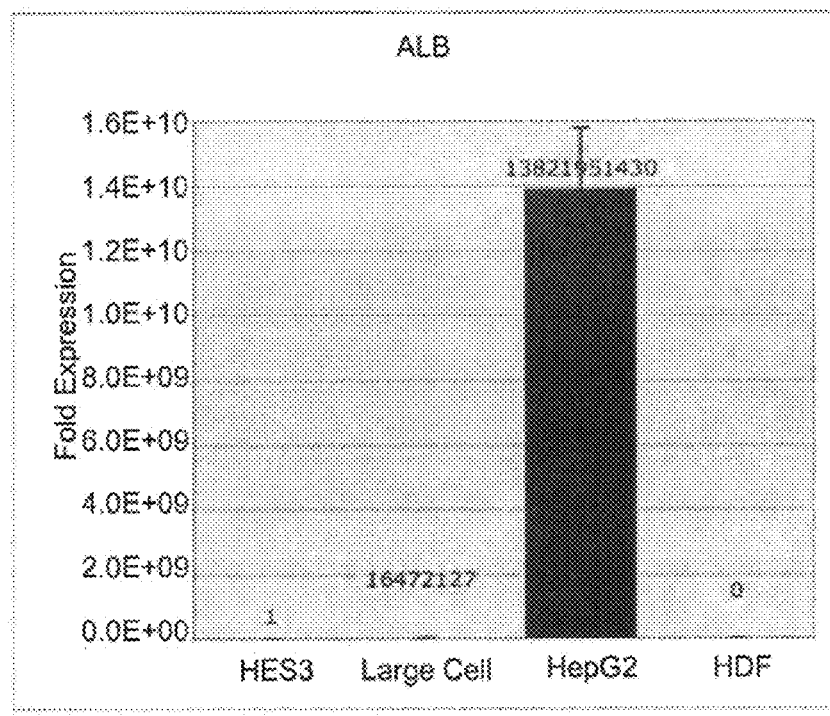
Figure 1G:
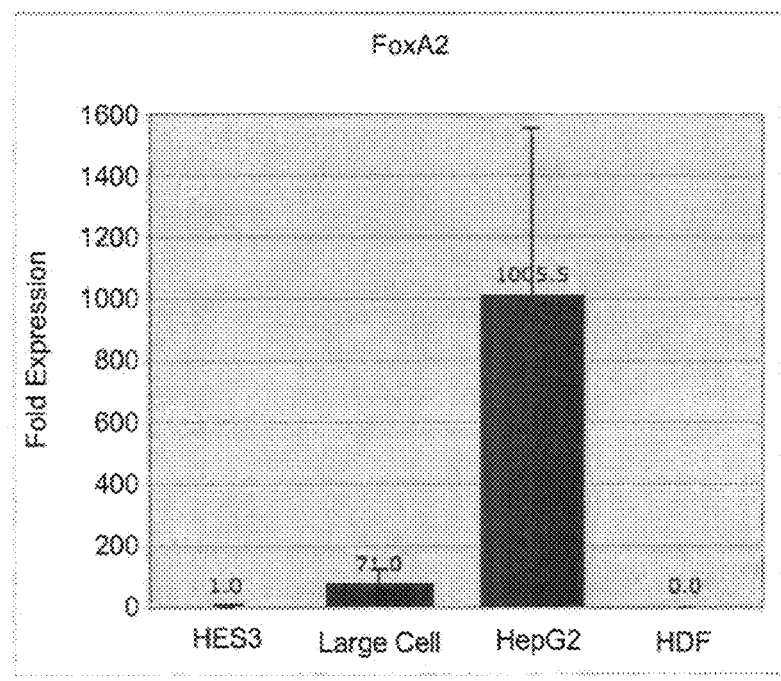
Figure 1H:
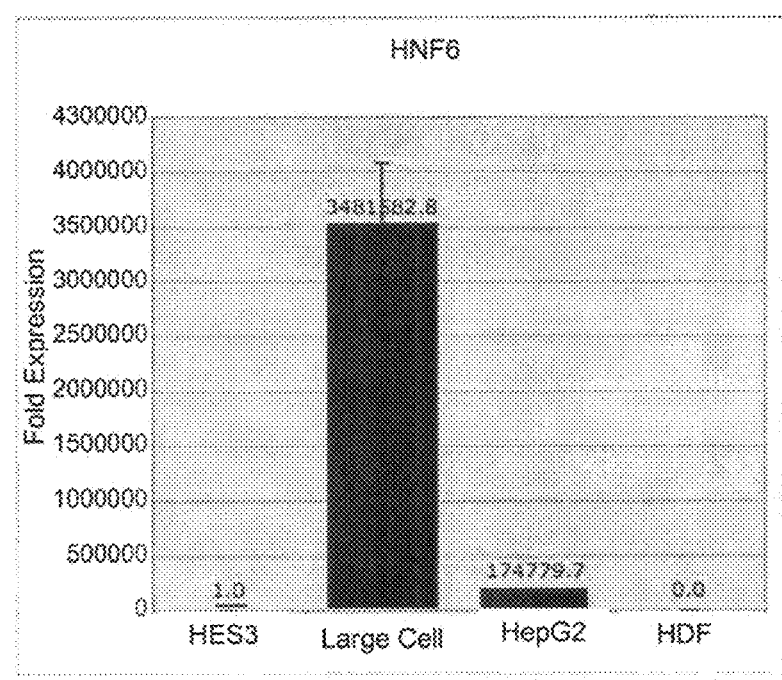
Figure 1I:
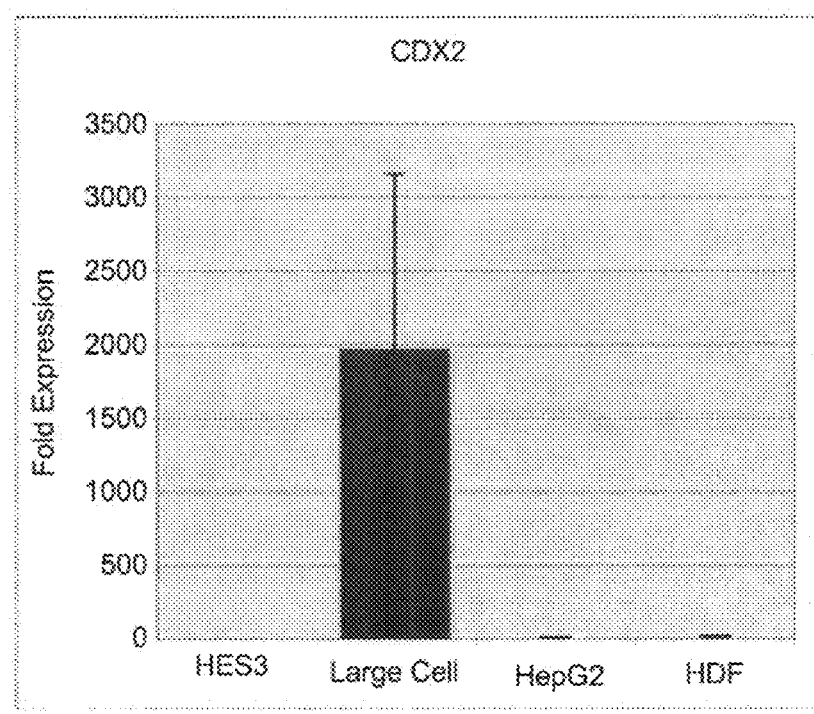
Figure 1J:
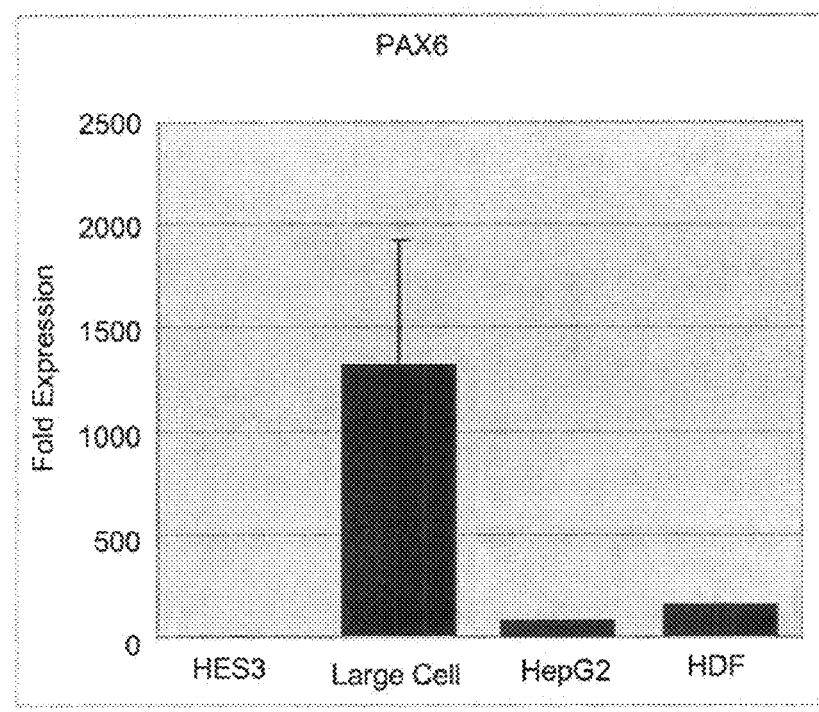
Figure 1K:
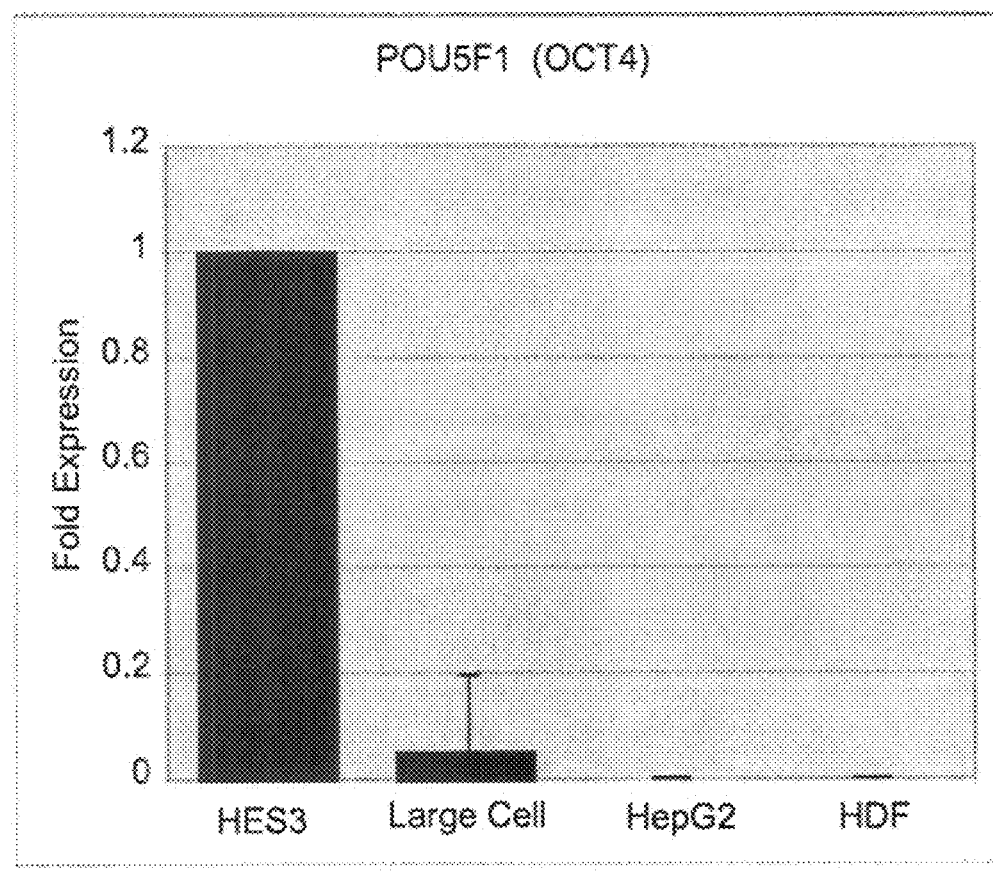

All references cited herein are incorporated by reference in their entirety as though fully set forth. Unless defined otherwise, technical and scientific terms used herein have the same meaning as commonly understood by one of ordinary skill in the art to which this invention belongs. Singleton at al., *Dictionary of Microbiology and Molecular Biology* 2nd ed., J. Wiley & Sons (New York, N.Y. 1994); March, *Advanced Organic Chemistry Reactions, Mechanisms and Structure* 4th ed., J. Wiley & Sons (New York, N.Y. 1992); and Sambrook and Russel, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described.

"Stem cell" as used herein refers to a cell that can continuously produce unaltered daughters and also has the ability to produce daughter cells that have different, more restricted properties. Stem cells include adult and ES cells.

"Progenitor cell" as used herein refers to a parent cell that gives rise to a distinct cell lineage by a series of cell divisions.

"Hepatocyte-like" cells as used herein includes liver cells, as well as cells that have attributes and characteristics of liver cells, such as the expression of markers associated with liver progenitor cells.

"HES2" and "HES3" as used herein refers to cell lines of human embryonic stem cells.

"Packaging material" as used herein refers to one or more physical structures used to house the contents of a kit, such as inventive compositions and the like. The packaging material is constructed by well known methods, preferably to provide a sterile, contaminant-free environment.

"Package" as used herein refers to a suitable solid matrix or material such as glass, plastic, paper, foil, and the like, capable of holding individual kit components. Thus, for example, a package can be a cryocontainer used to contain suitable quantities of peritoneal stem cells and/or peritoneal cells described herein. The packaging material generally has an external label which indicates the contents and/or purpose of the kit and/or its components.

As used herein, "FGF" means fibroblast growth factor.

As used herein, "MEK" (map-erk kinase), "MAPK" (mitogen-activated protein kinase) and "ERK" (extracellular signal-regulated kinase) refers to mitogen activated kinases.

As used herein, the term "MAPK/MEK/ERK signaling pathway" refers to a signal transduction pathway involving MAPK, MEK and ERK mitogen activated kinases, coupling intracellular responses to the binding of growth factors to cell surface receptors. The term MAPK/MEK/ERK signaling pathway includes the many protein components and kinase cascades that are part of the signaling pathway, as well as the various targets regulated by the pathway.

As used herein, the term "GSK" means glycogen synthase kinase 3 (GSK3).

As used herein, the term "BMP" means bone morphogenetic protein.

As readily apparent to one of skill in the art, any number of commercially and non commercially available molecules and compounds may be used to inhibit various signaling pathways and components referenced herein. For example, as used herein, FGF inhibitors include PD173074, PLX052, PKC412, AZD2171, Ki23057, BIBF1120, CHIR-258, Mastinib (AB1010), PHA739358, BMS-582664, AZD2171, PRO-001, Tyrphostin A46, and/or Tyrphostin B40. Similarly, MAPK/MEK/ERK signaling pathway inhibitors include PD98059, U0126, 5-Indotubercidin, /-Etema Zentaris, PD98059, AG 99, Apigenin, SP600125, 3-(2-Aminoethyl)-5-((4-ethoxyphenyl)methylene)-2,4-thiazolidinedione, SL327, SU4984, FR180204, SB203580, PD169316, SB202190, and/or ERK activation inhibitor peptides (such as Ste-PKKKPTPIQLNP—$NH_2$). Inhibitors of the GSK3 include BIO and related products, CT99021, Aloisine, RP106, Aloisine A, TDZD-8, OTDZT, AR-A014418, 7AIPM, Neurogenesis Inducer, TWS119, Kenpaullone (NSC-664704), Indirubin-3'-monoxime, GSK3b inhibitor peptide (such as Myr-N-GKEAPPAPPQSpP—$NH_2$), and/or Wnt signaling ligands (such as Wnt1 and/or Wnt3a). Inhibitors of BMP include LDN-193189, and/or BMP inhibitor proteins (such as Noggin, Chordin, Follistatin, and/or Wif).

As used herein, the term "PD184352" means Formula 1, a selective and non-competitive inhibitor of map-erk kinase 1.

(Formula 1)

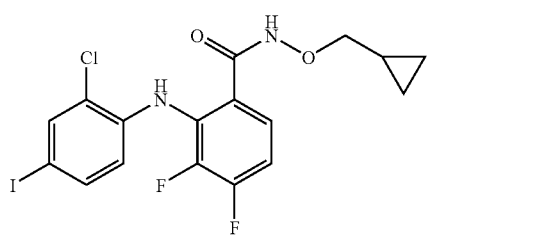

As used herein, the term "PD0325901" means Formula 2, a specific non-ATP-competitive inhibitor of map-erk kinase.

(Formula 2)

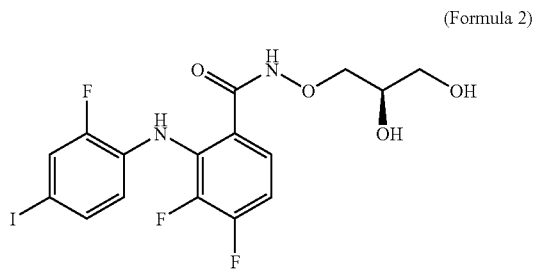

As used herein, the term "SU5402", or 3-[3-(2-Carboxyethyl)-4-methylpyrrol-2-methylidenyl]-2-indolinone, means Formula 3, an inhibitor of the tyrosine kinase activity of fibroblast growth factor receptor 1.

(Formula 3)

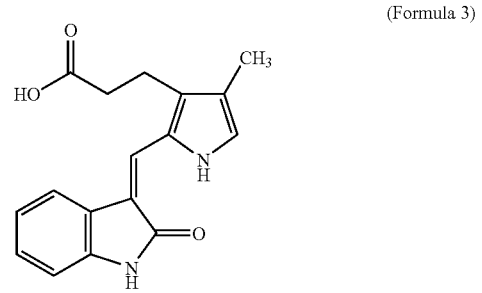

As used herein, the term "CHIR99021" means Formula 4, a selective inhibitor of GSK3β.

(Formula 4)

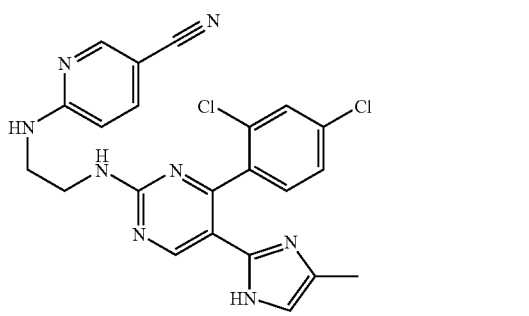

As disclosed herein, the inventors developed a method for the induction, isolation, and propagation of liver progenitor cells from human ES cell cultures or other human pluripotent stem cells, including induced pluripotent stem cells or pluripotent stem cells derived from fetal or adult tissues including germ cells. Human ES cell cultures, maintained as described previously in serum containing medium in the presence of fibroblast feeder cell support, were transferred to defined medium supplemented with small molecule inhibitors of MEK kinase, GSK-3, and FGF signaling. This combination of inhibitors has been shown to maintain pluripotency in cultures of mouse ES cells, but paradoxically, when added to cultures of human ES cells, it induces differentiation and the appearance of cells with morphology of primitive hepatocyte precursors. These cultures contain cells that are positive for the GCTM-5 antigen and may coexpress EpCAM and NCAM along with GCTM-5 on their surface. This combination of antigens enables the isolation of pure populations of progenitors from the differentiating cultures by flow cytometry or magnetic bead purification. These cells may also co-express markers of the bile duct lineage, such as cytokeratin 19, or markers of hepatocytes, such as amylase, albumin, or other liver specific gene products. The cells propagate and undergo expansion for prolonged periods in the presence of this medium described below, or in Kubota's medium, a minimal formulation previously shown to promote growth of adult liver progenitor cells in vitro. The cells are positive for surface markers characteristic of liver progenitor cells in the adult including the GCTM-5 antigen, Ep-CAM, and N-CAM. They are capable of differentiation into cells expressing markers of either bile duct or hepatocytes, such markers including albumin, transthyretin, cytochrome P450 enzymes. They show functional activity of adult liver cells such as indocyanine green dye uptake. They can give rise to mature hepatocytes either in vitro or following transplantation into liver damage models in vivo.

In one embodiment, the present invention provides a method of inducing and/or propagating liver progenitor cells by placing an ES cell culture in a medium supplemented with small molecule inhibitors of MEK kinase, GSK-3 and/or FGF signaling. In another embodiment, the ES cells are from a human. In another embodiment, the ES cell culture includes HES2 and/or HES3 cells.

In one embodiment, the present invention provides a method of inducing and/or propagating hepatocyte precursors by placing pluripotent stem cells in a medium supplemented with small molecule inhibitors of MEK kinase, GSK-3 and/or FGF signaling. In another embodiment, the pluripotent stem cells are induced pluripotent stem cells. In another embodiment, the pluripotent stem cells are derived from fetal and/or adult tissues. In another embodiment, the pluripotent stem cells are derived from germ cells. In another embodiment, the hepatocyte precursors may be used for in vitro studies of the pathogenesis of liver disease, including viral hepatitis. In another embodiment, the hepatocyte precursors are used for studies of metabolism and toxicity of drugs in vitro, including the development of predictive toxicology tests. In another embodiment, the hepatocyte precursors provide cells for transplantation therapy in liver diseases, including Hepatitis C. In another embodiment, the hepatocyte precursors express GCTM-5, EpCAM and/or NCAM. In another embodiment, the hepatocyte precursors express markers of the bile duct lineage. In another embodiment, markers of the bile duct lineage include cytokeratin 19. In another embodiment, the hepatocyte precursors express liver specific gene products, including amylase and/or albumin.

In one embodiment, the present invention provides a method of isolating progenitor cells by detecting the expression of GCTM-5, EpCAM and/or NCAM. In another embodiment, expression of GCTM-5, EpCAM and/or NCAM is detected by flow cytometry and/or magnetic bead purification.

In one embodiment, the present invention provides a method of isolating pure populations of progenitors from differentiating cultures by detecting the expression of GCTM-5, EpCAM, NCAM, markers of the bile duct lineage, and/or liver specific gene products. In another embodiment, expression is detected by flow cytometry and/or magnetic bead purification.

In one embodiment, the present invention provides a method of propagating adult liver cells by maintaining a stem cell culture in a 3i and/or Kubota medium. In another embodiment, the adult liver cells have the capacity of indocyanine green dye uptake.

In one embodiment, the present invention provides a method of transplanting mature hepatocytes into liver damage models by producing mature hepatocytes and transplanting the mature hepatocytes into liver damage models. In another embodiment, the mature hepatocytes are produced by transferring stem cells to a medium supplemented with small molecule inhibitors of MEK kinase, GSK-3 and/or FGF signaling. In another embodiment, the stem cells are human ES cells.

The present invention is also directed to kits for the induction, propagation and/or isolation of liver progenitor cells. The present invention is also directed toward kits for the transplantation of liver progenitor cells to liver damaged models.

Each kit is an assemblage of materials or components. The exact nature of the components configured in each inventive kit depends on its intended purpose. For example, some embodiments are configured for the purpose of inducing and/or propagating hepatocyte precursors.

Instructions for use may be included in the kit. "Instructions for use" typically include a tangible expression describing the technique to be employed in using the components of the kit for a desired purpose, such as for induction, propagation and/or isolation of liver progenitor cells.

Optionally, the kits also contain other useful components, such as those described herein, or buffers (e.g., PBS), growth media, tissue culture plates, multiple-well plates, flasks, chamber slides, differentiation media, stem cell media, goat serum, fetal bovine serum, basic fibroblast growth factor, epidermal growth factor, diluents, pharmaceutically acceptable carriers, syringes, catheters, applicators, pipetting or measuring tools, or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s).

One skilled in the art will recognize many methods and materials similar or equivalent to those described herein, which could be used in the practice of the present invention. Indeed, the present invention is in no way limited to the methods and materials described.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Inducing and Propagating Cells and Evidence of Adult Liver Stem Cells

The inventors previously identified a monoclonal antibody called GCTM-5. This reagent reacts with hepatoblasts, the precursors of bile ducts and hepatocytes, in the human embryonic liver. In the adult human liver, this antibody identifies a subset of bile duct cells in the termini of the biliary tree in the normal liver. In pathological states such as alcoholic cirrhosis, this population expands and can convert into cells co-expressing hepatocyte markers. The inventors also previously demonstrated that cells bearing the GCTM-5 antigen, and coreactive with liver specific markers such as amylase, albumin, and cytokeratin 19 could be induced in human ES cell cultures by specific modifications to the culture medium, including the use of low glucose basal medium containing low concentrations of serum supplemented with nicotinamide. The induction was slow and not efficient, the nature of these GCTM-5 positive cells was unknown, and they could not be serially cultivated. Here, the inventors describe important modifications to the procedure for inducing and propagating the cells and produce evidence that these cells are similar to adult liver stem cells.

Human ES cell cultures, maintained as described previously in serum containing medium in the presence of fibroblast feeder cell support, are transferred to defined medium supplemented with small molecule inhibitors of MEK kinase, GSK-3, and FGF signaling. This combination of inhibitors has been shown to maintain pluripotency in cultures of mouse ES cells but paradoxically, when added to cultures of human ES cells, it induces differentiation and the appearance of cells with morphology of primitive hepatocyte precursors. These cultures contain cells that are positive for the GCTM-5 antigen and may coexpress EpCAM and NCAM along with GCTM-5 on their surface. This combination of antigens enables the isolation of pure populations of progenitors from the differentiating cultures by flow cytometry or magnetic bead purification. These cells may also co-express markers of the bile duct lineage, such as cytokeratin 19, or markers of hepatocytes, such as amylase, albumin, or other liver specific gene products. The cells propagate and undergo expansion for prolonged periods in the presence of this medium described below, or in Kubota's medium, a minimal formulation previously shown to promote growth of adult liver progenitor cells in vitro. The cells are positive for surface markers characteristic of liver progenitor cells in the adult including the GCTM-5 antigen, Ep-CAM, and N-CAM. They are capable of differentiation into cells expressing markers of either bile duct or hepatocytes, such markers including albumin, transthyretin, cytochrome P450 enzymes. They show functional activity of adult liver cells such as indocyanine green dye uptake. They can give rise to mature hepatocytes either in vitro or following transplantation into liver damage models in vivo.

Example 2

Materials

HES2 or HES3 cells
MEF feeder seeded organ culture dishes

20% FCS hES medium
3i medium

| | |
|---|---|
| Neuro basal medium | 50% |
| DMEM/F-12 | 50% |
| N2 supplement | 1/200 v/v |
| B27 supplement | 1/100 v/v |
| 100 mM L-glutamine | 1/100 v/v |
| 0.1M β-ME | 1/1000 v/v |
| SU5402 (FGFR inhibitor) | 2 μM |
| PD184352 (ERK cascade inhibitor) | 0.8 μM |
| CHIR99021 (GSK3 inhibitor) | 3 μM |

MATRIGEL® (secreted gelatinous protein mixture) coated organ culture dish (1 hour coating using 1 ml of 1/30 DMEM/F-12-diluted BD MATRIGEL® (secreted gelatinous protein mixture) hESC-qualified Matrix).

Example 3

Procedure

HES2 or 3 cells were cultured for 5 days on MEF-feeders with 20% FCS hES medium in organ culture dishes. 20% FCS hES medium was replaced with 3i medium and cells were keeping culture in this medium for 3 days. Cells were detached as clumps by collagenase and feeder cells were removed by sedimentation in DMEM/F-12 medium.

Cells were seeded on MATRIGEL® (secreted gelatinous protein mixture) coated organ culture dish as 1 to 1 split and culture with 3i medium. After 3 to 5 days in culture, hepatoblast-like cells appeared. They were subsequently propagated using 3i or Kubota's medium following enzymatic dissection.

Example 4

Figure 2A:
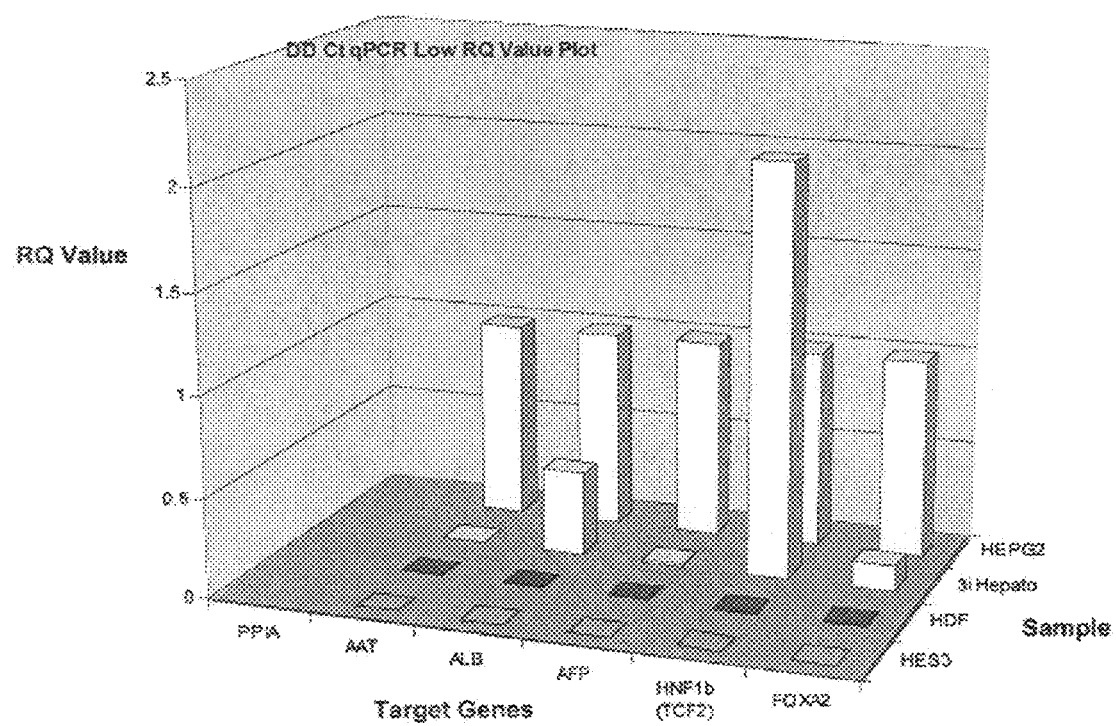
FIG. 2 depicts, in accordance with an embodiment herein, 3i media induced expression of (a) albumin and HNF1b and (b) HNF-6.
Figure 2B:
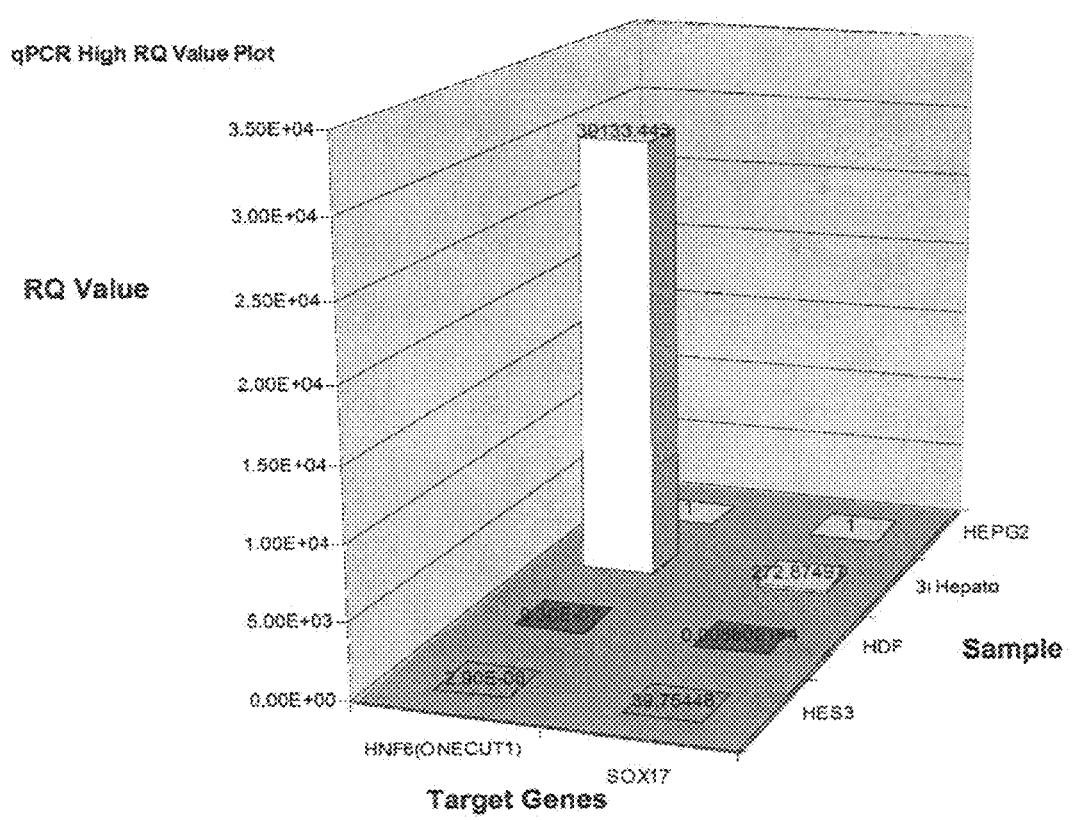
Figure 3:
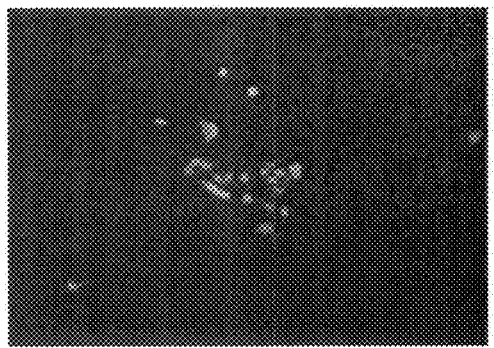
FIG. 3 depicts, in accordance with an embodiment herein, immunostaining for endoderm and liver markers.
Figure 3:
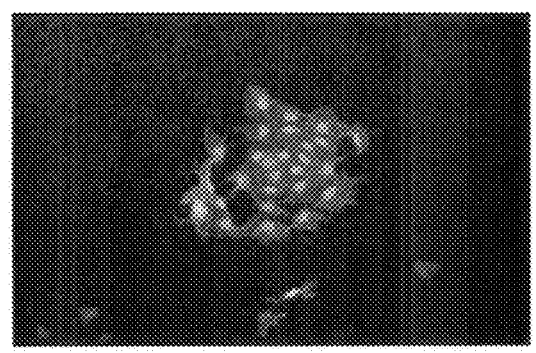
Figure 3:
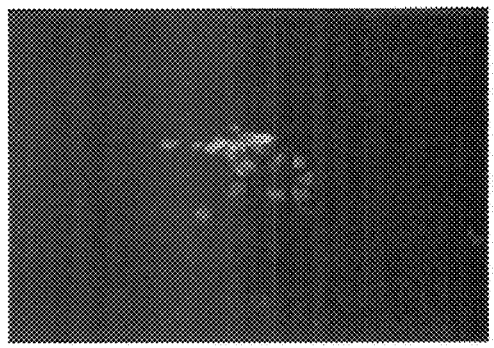

Gene Expression in Human Embryonic Stem Cells (hESC) Induced to Differentiate in 3-I Medium The inventors used QRT-PCR to examine gene expression in hESC cultures induced to differentiate using 3-I containing medium. Cells were transferred from stock cultures maintained under standard ES cell growth conditions, then placed in 2-I or 3-I medium. The cultures grown in the inducing medium containing cells of different morphology, with large cells resembling hepatoblasts. FIG. 1 shows that the large cells do not express pluripotency markers, but express markers of definitive endoderm (Sox-17), extraembryonic endoderm (Sox-7, Gata-4, AFP), and gut derivatives (Pax-6, pancreas; Cdx-2, intestine; albumin, liver; FoxA2 and HNF-6, liver progenitors). The striking induction of albumin, HNF-6, and HNF-1, compared to AFP, suggests the population may contain bipotent bile duct and hepatocyte progenitors (FIGS. 2a and b). FIG. 3 shows immunostaining for HNF3 beta, Sox-17, and albumin. The 2-I or 3-I cultures induce endodermal differentiation in the hESC cultures, and the cultures strongly express markers of liver progenitors. Further modification of the culture system, including suppression of BMP and insulin/IGF signaling early on, enhanced the yield of definitive endoderm and liver progenitors.

Example 5

Figure 4A:
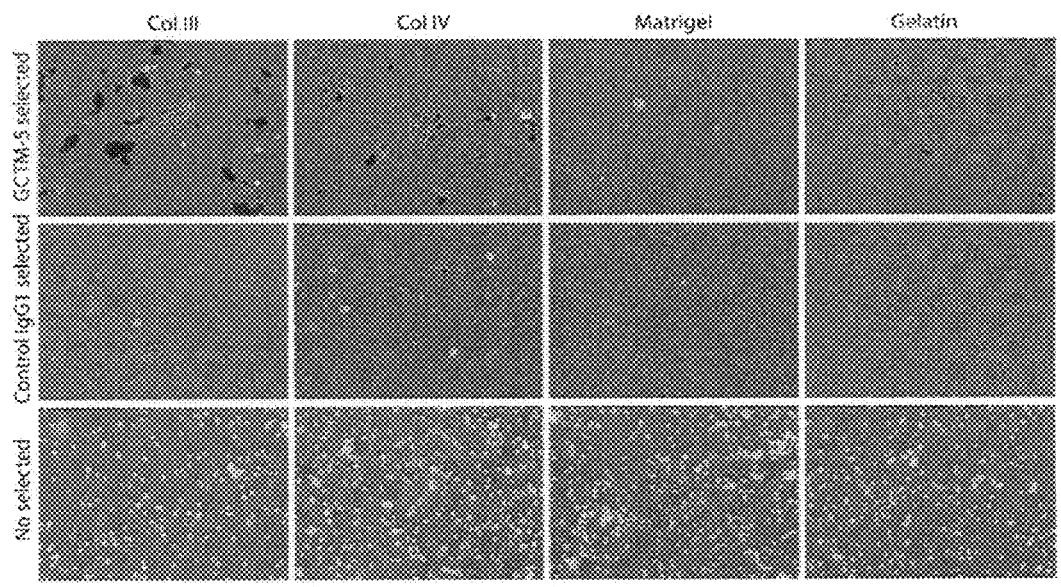
FIG. 4 depicts, in accordance with an embodiment herein, isolation and attachment of GCTM-5 positive cells from adult liver, including (a) Day 4 in Kubota's media+bFGF 5 ng/ml, and (b) Day 13 in Kubota's media+bFGF 5 ng/ml.
Figure 4B:
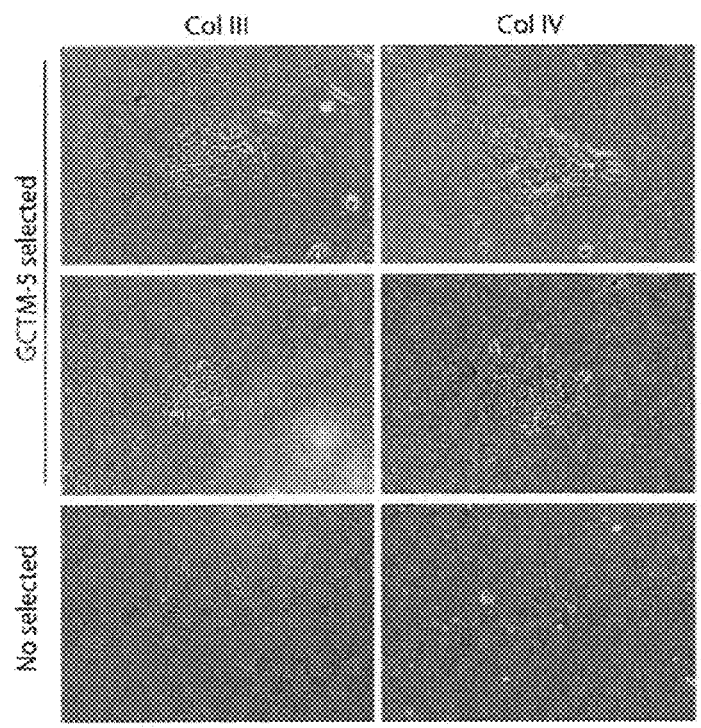

Isolation, Culture and Characterization of GCTM-5 Positive Cells from the Nonparenchymal Fraction of Adult Human Liver The inventors believed that the 3-I induced cultures might contain cells showing similar patterns of gene expression to the GCTM-5 positive cells in the adult liver. Study of the growth requirements of these adult liver cells might enhance our ability to propagate the 3-I induced liver progenitors directly. Therefore, the inventors further characterized GCTM-5 positive cells isolated from the non-parenchymal fraction of the adult human liver. In previous work, GCTM-5 cells isolated from adult liver were grown under conditions that supported only bile duct differentiation, and this differentiation was observed under those conditions (1). We plated freshly isolated adult non-parenchymal cells into a modified culture system that was designed to promote expansion of bipotent liver progenitor cells. Cells were isolated using magnetic bead immunoaffinity, then placed into culture in modified Kubota's medium on collagen type III or IV in the presence of FGF-2. Under these conditions, the cells attached and formed microcolonies which expanded for up to four weeks (FIG. 4).

MATRIGELO®(secreted gelatinous protein mixture) failed to support robust attachment and colony formation of the GCTM-5 positive cells. Contrary to previous reports these cells could not be serially cultivated using the Kubota's medium. Because the cells could not be serially cultivated, the inventors examined expression of receptor associated kinase genes using a low density QRTPCR array, with a view towards discovering additional factors that might help expand the population in vitro.

Example 6

Kinase Array Analysis of GCTM-5 Positive Cells from the Non-Parenchymal Fraction of Adult Liver and 3-I Induced Human Embryonic Stem Cells Unfractionated liver non-parenchymal cells were compared with GCTM-5 positive cells, GCTM-5 negative cells (essentially the same as the unfractionated population), and 3-I cells for their expression of kinases. Kinases that were expressed in all fractions and enriched in the GCTM-5 positive fraction included the following: ACVR1B, BMP2R, EGFR, ERBB2, ERBB3, FGFR1, FGFR2, FGFR3, IGFR1, INSR, KDR, TEK, TGFBR1, TGFBR2. Because the 3-I cells in this experiment were not fractionated, it was not expected that their patterns of gene expression would be similar to those of adult liver GCTM-5 positive cells. The results suggested that Activin, BMP, EGF, heregulin, FGF-1, IGF, VEGF, angiopoietin, and TGF beta might stimulate growth or differentiation of the GCTM-5 positive cells.

Example 7

Methods: 3i-Induction of Hepatocyte-Like Cells—Materials HES2 or HES3 Cells

Organ culture dishes seeded with Mouse embryo fibroblast feeder cells Human embryonic stem cell medium containing 20% fetal calf serum (2) 3i* or new 3i** medium
 Neuro basal medium 50%
 DMEM/F-12 50%
 N2 supplement 1/200 v/v
 B27 supplement 1/100 v/v
 100 mM L-glutamine 1/100 v/v
 0.1M β-ME 1/1000 v/v
 *SU5402 (FGFR inhibitor) 2 μM
 *P0184352 (ERK cascade inhibitor) 0.8 μM
 **PD0325901 (MAPK inhibitor) 0.4 μM
 CHIR99021 (GSK3 inhibitor) 3 μM
 **Dorsomorphin (BMP cascade inhibitor) 2 μM MATRIGEL® (secreted gelatinous protein mixture) coated organ culture dish (Coated for one hours with 1 ml of 1/30 DMEM/F-12-diluted BD MATRIGEL® (secreted gelatinous protein mixture) hESC-qualified Matrix).

Example 8

Methods: 3i-Induction of Hepatocyte-Like Cells—Procedure

HES2 or 3 cells were cultured 5 days on MEF-feeders with 20% FCS hES medium in organ culture dishes. 20% FCS hES medium was replaced with 3i medium and cells were maintained in this medium for 2 days.

Cells were detached as clumps by collagenase and feeder cells were removed by sedimentation in DMEM/F-12 medium.

Cells were seeded on MATRIGELO® (secreted gelatinous protein mixture) coated organ culture dish as 1 to 1 split and culture with 3i medium.

After 3 to 5 day culture, the hepatocyte-like cells appeared.

Example 9

Methods: qPCR Analysis

The induced hepatocyte-like cells were marked and picked manually into microtubes. Undifferentiated HES3 cells and human dermal fibroblast cells were collected as negative controls, and HepG2 cells were collected as a positive control cell. The Cells were lysed and total RNA was purified by RNA Easy Micro kit (Qiagen) with on column Dnase-treatment. Then cDNA was synthesized from 1 µg total RNA by random hexamer priming using an OmniScript kit (Quiagen). The cDNA was diluted 8 fold into water and 2× TaqMan PCR master mix and TaqMan Gen Expression Assay Mix were added (Applied Biosystems). PCR were performed on an ABI prism 7900 instrument (Applied Biosystems). The data was analyzed with delta CT method by RQ manager software (Applied Biosystems). All qPCR reaction were duplicated in each experiment and analysis were performed analyzed with triplicate experiments.

TaqMan Gene Expression Assays:
Gene AssayID Expression
Cyclophilin (PPIA) Hs99999904_m1 Ubiquitous (Endogeneous control)
OCT3/4 (POU5F1) Hs01895061_u1 Undifferentiated cells
GATA4 Hs00171403_m1 Early definitive/extraembryonic Endoderm
T (Brachyury) Hs00610080_m1 Early mesoendoderm/mesoderm
SOX7 Hs00846731_s1 Early extraembryonic Endoderm
SOX17 Hs00751752_s1 Early definitive Endoderm
CDX2 Hs00230919_m1 Early trophectoderm/gut endoderm
PAX6 Hs00240871_m1 Neuroectoderm/early pancreatic cells
FOXA2 (HNF3) Hs00232764_m1 Early liver cells
HNF6 (ONECUT1) Hs00413554_m1 Early liver cells
AFP Hs01040597_m1 Early liver cells/extraembryonic Endoderm
ALB (Albumin) Hs00609403_m1 Hepatoblast/Placenta

Example 10

Methods: GCTM-5 Positive Cells Isolation

Human liver non-parenchymal cells, supplied by CellzDirect/Life Technologies. Were collected into 50 ml tubes (10E8 cells/tube). The cells were suspended with buffer 1 (0.1% BSA/2 mM EDTA/PBS(−)), and centrifuged 1000 rpm 5 minutes, and this washing step was repeated until the supernatant were clear (around 3 times). GCTM-5 antibody or control IgG1 were added as 1 ||g/10E6 cells (100 µg/50 ml buffer 1/tube), and incubated with gentle rotation at 4° C. for 1 hour. The cells were collected by centrifugation and non-reacted antibody was washed out by 3 times with buffer 1 and centrifugation. Then cells were suspended with 10 ml buffer 1/tube and magnetic beads-conjugated secondly antibodies (Dynabeads Rat anti-Mouse IgG1: Dynal Biotech) were added as 10 µl/10 E7 cells (100 µl/10 ml buffer 1/tube), and then incubated with gentle rotation at 4° C. 1 hour. The cell suspension was transferred into 1.5 ml microtubes. The tubes were placed in the magnet stand, the supernatant was discarded, and the cell pellets in the tube walls were resuspended with buffer 1. The washing step with buffer 1 were repeated 3 times and then washed with culture medium once. The cell pellets were resuspended with culture medium and seeded onto culture plates, or directly lysed with Trysol (Invitorogen) for RNA purification.

Example 11

Methods: TaqMan Human Protein Kinase Array Analysis

The GCTM-5 positive, negative, non-selected cell total RNA were purified as a magnet bead-free pellet in Trysol (Invitrogen). The pre-purified total RNA was re-purified by RNA easy micro kit with on column Dnase treatment (Qiagen). The 3i-induced hapatocyte-like cell RNA was purified as described above. Then cDNA was synthesized from 2 µg total RNA by OmniScript kit (Quiagen) with random hexamer primers. The cDNA was diluted 10 times by water, 2× TaqMan PCR master mix was, and samples were then loaded onto TaqMan Human Protein Kinase Array (4367784: Applied Biosystems). PCR reactions were performed on the ABI prism 7900 (Applied Biosystems). The data was analyzed with the delta delta CT method by RQ manager software (Applied Biosystems). The experiments were duplicated to confirm the results.

Example 12

Various FGF/MEK/ERK, GSK3b and BMP Signaling Inhibitors May Be Utilized for the Induction and Selection of Endoderm Cells Induction and selection of endoderm cells via:
FGF/MEK/ERK inhibition—inhibit ES cell self-renewal and induce differentiation, inhibit neural and trophectodermal cell growth.
GSK3b inhibition—induce mesoderm/endoderm differentiation.
Serum starvation—inhibit mesoderm/mesenchymal cell growth.
BMP inhibition (optionally)—inhibit extraembryonic cell differentiation.

The FGF/MEK/ERK signaling pathway includes several molecules, such as FGF, FGFR, FRS, GRB, SOS, RAS, RAF, MEK, ERK, etc. All of these molecules may be utilized as potential targets to inhibit this pathway. Additionally, GSK3b inhibition means that the induction of the Wnt signaling pathway could also be utilized for the same purpose. This, in turn, would include Wnt signaling inhibitory molecules, such as GSK3b, Axin, APC, which could also be potential targets.

Numerous examples of FGFR/MEK/ERK signaling inhibitors and GSK3b inhibitors exist, both commercially and noncommerically. Some examples include the following:

FGFR inhibitors: PD173074, PLX052, PKC412, AZD2171, Ki23057, BIBF1120, CHIR-258, Mastinib (AB1010), PHA739358, BMS-582664, AZD2171, PRO-001, Tyrphostin A46, Tyrphostin B40.

MAPK/MEK(MAPKK)/ERK pathway inhibitors: PD98059, U0126, 5-Indotubercidin, /-Eterna Zentaris, PD98059; AG 99, Apigenin, SP600125, 3-(2-Aminoethyl)-5-((4-ethoxyphenyl)methylene)-2,4-thiazolidinedione, SL327, SU4984, FR180204, SB203580, PD169316, SB202190, ERK activation inhibitor peptides (such as Ste-PKKKPTPIQLNP—NH$_2$).

GSK3b inhibitors: BIO and related products, CT99021, Aloisine, RP106, Aloisine A, TDZD-8, OTDZT, AR-A014418, 7AIPM, Neurogenesis Inducer, TWS119, Kenpaullone (NSC-664704), Indirubin-3'-monoxime, GSK3b inhibitor peptide (such as Myr-N-GKEAPPAP-PQSpP—NH$_2$), Wnt signaling ligands (such as Wnt1 and/or Wnt3a).

BMP inhibitors: LDN-193189, BMP inhibitor proteins (such as Noggin, Chordin, Follistatin, and/or Wif).

Example 13

3i, Alternative 3i and 2i Medium
Components—Dosages Examined (1) In combination of SU5402, PD184352 and CHIR99021:
SU5402: 1 µM decreased hepatic differentiation and increased trophectodermal/neural cells; 2 µM most efficient; 4 µM toxic.
PD 184352: 0.4 µM decreased hepatic differentiation and increased trophectodermal cells; 0.8 µM most efficient, 1.6 µM no difference from 0.8 µM
CHIR99021: 1.5 µM dramatically decreased hepatic differentiation/growth; 3 µM most efficient; 6 µM some kind of non-hepatic cells grow very well.
(2) In combination of PD0325901 and CHIR99021:
PD0325901; 0.4 µM no difference from 3i, 0.8 µM more efficient than 3i, 1.6 µM no difference from 0.8 µM
(3) In combination of PD0325901, CHIR99021 and Dorsomorphin:
Dorsomorphin: 1 µM slightly inhibit extraembryonic cell differentiation without disturbing hepatic differentiation; 2 µM greatly inhibit extraembryonic cell differentiation without disturbing hepatic differentiation; 5 µM toxic.

While the description above refers to particular embodiments of the present invention, it should be readily apparent to people of ordinary skill in the art that a number of modifications may be made without departing from the spirit thereof. The accompanying claims are intended to cover such modifications as would fall within the true spirit and scope of the invention. The presently disclosed embodiments are, therefore, to be considered in all respects as illustrative and not restrictive.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventor that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Accordingly, the invention is not limited except as by the appended claims.

REFERENCES

1. Stamp L, Crosby H A, Hawes S M, Strain A J, & Pera M F (2005) A novel cellsurface marker found on human embryonic hepatoblasts and a subpopulation of hepatic biliary epithelial cells. Stem cells (Dayton, Ohio) 23(1):103-112.

2. Reubinoff B E, Pera M F, Fong C Y, Trounson A, & Bongso A (2000) Embryonic stem cell lines from human blastocysts: somatic differentiation in vitro. Nat Biotechnol 18(4):399-404.
3. Ying Q, Wray J, Nichols J, Batlle-Morera L, Doble B, Woodgett J, Cohen P, Smith A (2008) The ground state of embryonic stem cell self-renewal. Nature Vol 453: 519-523.

The invention claimed is:

1. A method of inducing human hepatocyte cells from human embryonic stem cells, comprising:
   a) providing a quantity of human embryonic stem (hES) cells;
   b) placing the hES cells on an extracellular matrix and in a medium containing one of:
      i) neurobasal medium, DMEM, N2, B27, L-glutamine, β-ME, SU5402, PD184352, and CHIR99021,
      ii) neurobasal medium, DMEM, N2, B27, L-glutamine, β-ME, SU5402, PD184352, CHIR99021 and dorsomorphin, or
      iii) neurobasal medium, DMEM, N2, B27, L-glutamine, β-ME, PD0325901, CHIR99021, and dorsomorphin; and
   c) culturing the hES cells to form hepatocyte cells.

2. The method of claim 1, wherein the medium containing
   i) neurobasal medium, DMEM, N2, B27, L-glutamine, β-ME, SU5402, PD184352, and CHIR99021, comprises a concentration of about 1 to about 6 μM SU5402.

3. The method of claim 2, wherein the SU5402 is about 2 μM.

4. The method of claim 1, wherein the medium containing
   i) neurobasal medium, DMEM, N2, B27, L-glutamine, β-ME, SU5402, PD184352, and CHIR99021, comprises a concentration of about 0.2 to about 3.0 μM PD184352.

5. The method of claim 4, wherein the PD184352 is about 0.8 μM.

6. The method of claim 1, wherein the medium containing
   i) neurobasal medium, DMEM, N2, B27, L-glutamine, β-ME, SU5402, PD184352, and CHIR99021, comprises a concentration of about 1 to about 6 μM CHIR99021.

7. The method of claim 6, wherein the CHIR99021 is about 3 μM.

8. The method of claim 1, wherein the medium containing
   ii) neurobasal medium, DMEM, N2, B27, L-glutamine, β-ME, SU5402, PD184352, CHIR99021 and dorsomorphin, comprises a concentration of about 1 to about 6 μM SU5402.

9. The method of claim 8, wherein the SU5402 is about 2 μM.

10. The method of claim 1, wherein the medium containing
    ii) neurobasal medium, DMEM, N2, B27, L-glutamine, β-ME, SU5402, PD184352, CHIR99021 and dorsomorphin, comprises a concentration of about 0.2 to about 3.0 μM PD184352.

11. The method of claim 10, wherein the PD184352 is about 0.8 μM.

12. The method of claim 1, wherein the medium containing
    ii) neurobasal medium, DMEM, N2, B27, L-glutamine, β-ME, SU5402, PD184352, CHIR99021 and dorsomorphin, comprises a concentration of about 1 to about 6 μM CHIR99021.

13. The method of claim 12, wherein the CHIR99021 is about 3 μM.

14. The method of claim 1, wherein the medium containing
    ii) neurobasal medium, DMEM, N2, B27, L-glutamine, β-ME, SU5402, PD184352, CHIR99021 and dorsomorphin, comprises a concentration of about 1 to about 6 μM dorsomophin.

15. The method of claim 14, wherein the dorsomorphin is about 3 μM.

16. The method of claim 1, wherein the medium containing
    iii) neurobasal medium, DMEM, N2, B27, L-glutamine, β-ME, PD0325901, CHIR99021, and dorsomorphin; comprises a concentration of about 0.2 to about 3.0 μM PD0325901.

17. The method of claim 16, wherein the PD0325901 is about 0.8 μM.

18. The method of claim 1, wherein the medium containing
    iii) neurobasal medium, DMEM, N2, B27, L-glutamine, β-ME, PD0325901, CHIR99021, and dorsomorphin comprises a concentration of about 1 to about 6 μM CHIR99021.

19. The method of claim 18, wherein the CHIR99021 is about 3 μM.

20. The method of claim 1, wherein the medium containing
    iii) neurobasal medium, DMEM, N2, B27, L-glutamine, β-ME, PD0325901, CHIR99021, and dorsomorphin comprises a concentration of about 1 to about 6 μM dorsomophin.

21. The method of claim 20, wherein the dorsomophin is about 3 μM.

* * * * *